(12) United States Patent
Holman (10) Patent No.: US 10,974,022 B2
(45) Date of Patent: Apr. 13, 2021

(54) NASAL IMPLANT ASSEMBLY (71) Applicant: Gyrus ACMI, Inc., Southborough, MA (US)

(72) Inventor: Thomas J. Holman, Princeton, MN (US)

(73) Assignee: Gyrus Acmi, Inc., Southborough, MA (US)

( * ) Notice: Subject to any disclaimer, the term of this patent is extended or adjusted under 35 U.S.C. 154(b) by 213 days.

(21) Appl. No.: 15/907,407

(22) Filed: Feb. 28, 2018

(65) Prior Publication Data

US 2019/0262578 A1    Aug. 29, 2019

(51) Int. Cl.
*A61M 25/00* (2006.01)
*A61N 2/00* (2006.01)
(Continued)

(52) U.S. Cl.
CPC ........ *A61M 25/0017* (2013.01); *A61K 31/58* (2013.01); *A61L 29/04* (2013.01); *A61L 29/106* (2013.01); *A61L 29/146* (2013.01); *A61L 29/16* (2013.01); *A61L 31/082* (2013.01); *A61L 31/146* (2013.01); *A61L 31/16* (2013.01); *A61M 25/0068* (2013.01); *A61M 25/0097* (2013.01); *A61M 39/02* (2013.01); *A61N 2/004* (2013.01);
(Continued)

(58) Field of Classification Search
CPC ...... A61L 31/082; A61L 31/16; A61L 29/106; A61L 29/146; A61L 31/146; A61L 29/16; A61L 2300/41; A61L 29/04; A61M 2025/0057; A61M 39/02; A61M 2210/0681; A61M 2039/0205; A61M 25/0068; A61M 25/0017; A61M 2205/0272; A61M 2205/04; A61M 25/0097; A61P 11/02; A61N 2/004; A61K 31/58
USPC ...................................................... 600/9–15
See application file for complete search history.

(56) References Cited

U.S. PATENT DOCUMENTS 5,921,244 A    7/1999 Chen et al.
6,673,104 B2   1/2004 Barry
(Continued)

OTHER PUBLICATIONS

"Stent hypersensitivity and infection in sinus cavities" Nicholas G. Kounis, M.D., Ph.D., George D. Soufras, M.D., Ph.D., and George Hahalis, M.D., Ph.D. Allergy Rhinol (Providence). 2013 Fall; 4(3): e162-e165. (Year: 2013).*

*Primary Examiner* — Navin Natnithithadha
*Assistant Examiner* — Sunita Reddy
(74) *Attorney, Agent, or Firm* — Schwegman Lundberg & Woessner, P.A.

(57) ABSTRACT

Provided is a nasal implant assembly comprising a hollow implant having a distal end and a proximal end, the distal end configured to have a segment deposited with magnetic particles; and a medical syringe configured to be attachable to the proximal end of the hollow implant and also configured to be capable of retaining and transporting a magnetically active fluid composition through the implant to a nasal cavity of a subject. Also provided is a method of treating chronic rhinosinusitis in a subject, the method comprising the steps of positioning a nasal implant having magnetic particles into a nasal cavity; loading a medical syringe with a magnetically active fluid composition; and transporting the loaded magnetically active fluid composition to the nasal cavity to treat chronic rhinosinusitis.

18 Claims, 5 Drawing Sheets

(51) Int. Cl.
*A61M 39/02* (2006.01)
*A61L 29/04* (2006.01)
*A61L 29/14* (2006.01)
*A61L 29/16* (2006.01)
*A61L 29/10* (2006.01)
*A61P 11/02* (2006.01)
*A61K 31/58* (2006.01)
*A61L 31/08* (2006.01)
*A61L 31/14* (2006.01)
*A61L 31/16* (2006.01)

(52) U.S. Cl.
CPC ........... *A61P 11/02* (2018.01); *A61L 2300/41* (2013.01); *A61M 2025/0057* (2013.01); *A61M 2039/0205* (2013.01); *A61M 2205/0272* (2013.01); *A61M 2205/04* (2013.01); *A61M 2210/0681* (2013.01)

(56) References Cited

U.S. PATENT DOCUMENTS

| | | | | |
|---|---|---|---|---|
| 2002/0037919 A1* | 3/2002 | Hunter | .................. | A61K 31/047 514/449 |
| 2002/0133219 A1* | 9/2002 | Barry | ..................... | A61F 2/91 623/1.15 |
| 2004/0096511 A1* | 5/2004 | Harburn | ................ | A61K 9/0009 424/489 |
| 2005/0240147 A1* | 10/2005 | Makower | ................ | A61B 17/24 604/96.01 |
| 2005/0281858 A1* | 12/2005 | Kloke | ..................... | A61L 27/34 424/423 |
| 2006/0004286 A1* | 1/2006 | Chang | ..................... | A61B 5/06 600/435 |
| 2006/0004323 A1* | 1/2006 | Chang | ..................... | A61B 17/24 604/28 |
| 2006/0041182 A1* | 2/2006 | Forbes | ..................... | A61F 2/82 600/12 |
| 2006/0095066 A1* | 5/2006 | Chang | ................ | A61B 17/1204 606/199 |
| 2006/0142632 A1* | 6/2006 | Meretei | ............... | A61B 17/3207 600/12 |
| 2006/0165805 A1* | 7/2006 | Steinhoff | ........... | A61K 48/0075 424/489 |
| 2006/0210605 A1* | 9/2006 | Chang | ..................... | A61B 17/24 424/434 |
| 2007/0231393 A1* | 10/2007 | Ritter | ..................... | A61K 9/0009 424/489 |
| 2007/0269385 A1* | 11/2007 | Yun | ......................... | A61K 31/22 424/45 |
| 2008/0124400 A1* | 5/2008 | Liggins | ..................... | A61K 9/16 424/501 |
| 2009/0062828 A1* | 3/2009 | Marr | ................ | A61B 17/00234 606/159 |
| 2009/0299127 A1* | 12/2009 | Rudolph | ................ | A61K 31/65 514/1.1 |
| 2010/0028402 A1* | 2/2010 | Dobrovolskaia | ........ | A61L 31/16 424/423 |
| 2013/0204120 A1* | 8/2013 | Weinberg | ............... | A61N 2/004 600/411 |
| 2015/0088098 A1* | 3/2015 | Lane | ..................... | A61M 3/0279 604/514 |
| 2015/0150714 A1* | 6/2015 | Anikeeva | ................. | A61F 7/00 607/103 |
| 2015/0366999 A1* | 12/2015 | Amritphale | ........ | A61K 49/0438 600/429 |
| 2016/0158570 A1* | 6/2016 | Khizroev | ............... | A61N 2/006 600/12 |
| 2019/0046488 A1* | 2/2019 | Rosenblatt | ............. | A61K 45/06 |

\* cited by examiner

NASAL IMPLANT ASSEMBLY

FIELD

The present disclosure generally relates to a nasal implant assembly for concentrating a drug substance around a nasal cavity of a patient. More specifically, the present disclosure relates to a nasal implant assembly for concentrating a drug substance around a nasal cavity through magnetic attractions to treat chronic rhinosinusitis of a patient.

BACKGROUND

Chronic rhinosinusitis (CRS) is a persistent symptomatic inflammation of the nasal and paranasal sinuses characterized by at least 8-12 weeks of two or more symptoms including nasal congestion or blockage, anterior or posterior nasal discharge, facial pressure or pain, and reduction or loss of smell. CRS can be brought on by an infection, by growths in the sinuses (nasal polyps) or by a deviated nasal septum. It most commonly affects young and middle-aged adults, but can also affect children. CRS is thus considered a public health problem having a significant social and economic impact.

Despite decades of world-wide effort toward discovery of therapeutic approaches against CRS, effective treatment options for this disease remain limited in scope and largely inadequate.

Accordingly, there is an ongoing need for improved devices and methods for an effective treatment of chronic rhinosinusitis.

SUMMARY

In one embodiment, the present disclosure provides a nasal implant comprising a hollow structure having a distal end and a proximal end, the distal end configured to include magnetic particles, and the proximal end configured to be attachable to a container, an injector, or a medical syringe.

In one embodiment, the present disclosure provides a medical assembly for nasal implantation of an implant into a patient, the assembly comprising: the implant having a distal end and a proximal end, the distal end configured to include magnetic particles; and a container, an injector, or a medical syringe configured to be attachable to the proximal end of the implant.

In one embodiment, the present disclosure provides a drug delivery assembly for delivering a drug substance to a nasal cavity of a subject, the assembly comprising: a hollow implant having a distal end and a proximal end, the distal end configured to include magnetic particles; and a container, an injector, or a medical syringe configured to be capable of retaining and transporting a magnetically active or magnetizable fluid composition containing the drug substance.

In an embodiment, the present disclosure provides a method of treating chronic rhinosinusitis of a subject. The method includes a step of positioning a nasal implant in a nasal cavity. The method also includes a step of delivering a magnetically active fluid composition to the nasal cavity through the nasal implant wherein the magnetically active fluid composition contains a pharmaceutically active drug substance.

In an embodiment, the present disclosure provides a method of treating chronic rhinosinusitis of a subject, the method comprising the steps of: positioning a nasal implant in a nasal cavity; delivering a magnetically active fluid composition to the nasal cavity through the nasal implant, wherein the magnetically active fluid composition contains a pharmaceutically active drug substance.

In an embodiment, the present disclosure also provides a method of treating chronic rhinosinusitis of a subject, comprising providing a nasal implant comprising a hollow implant having a segment deposited with magnetic particles; providing a container, an injector, or a medical syringe configured to be capable of retaining and transporting a magnetically active fluid composition containing a drug substance; and transporting the magnetically active spheres/composition to the nasal implant from the container, the injector, or the medical syringe.

In an embodiment, the present disclosure provides a method of concentrating a drug substance around a nasal cavity of a patient, the method comprising: providing an implant configured to have a distal end deposited with magnetic particles; providing a medical syringe configured to be capable of retaining and transporting a magnetically active fluid composition containing a drug substance; inserting the implant into the nasal cavity; connecting or engaging the implant with the medical syringe; loading the magnetically active fluid composition into the medical syringe; and transporting the magnetically active fluid composition to the nasal cavity to provide increased concentration of the drug substance around the nasal cavity.

In another embodiment, the present disclosure provides a method of treating chronic rhinosinusitis of a patient by concentrating a drug substance around a nasal cavity that needs treatment, the method comprising providing a nasal implant comprising a hollow implant having a segment deposited with magnetic particles; providing a medical syringe configured to be capable of retaining and transporting a magnetically active fluid composition containing a drug substance; providing the magnetically active fluid composition containing the drug substance; inserting the nasal implant into the nasal cavity; loading the magnetically active fluid composition into the medical syringe; pushing the fluid composition through the medical syringe to the nasal cavity to treat chronic rhinosinusitis.

In another embodiment, the present disclosure also provides a kit for performing a method as described herein. The kit includes a nasal implant, a container, injector, or syringe, a magnetically active fluid composition containing a drug substance, and other accessories and instructions for delivering the implant and the magnetically active fluid composition into a nasal cavity of a patient.

DETAILED DESCRIPTION

The explanations and illustrations presented herein are intended to acquaint others skilled in the art with the disclosure, its principles, and its practical applications. Those skilled in the art may adapt and apply the disclosure in numerous forms, as may be best suited to the requirements of a particular use. The specific embodiments of the present disclosure as set forth are not intended to be exhaustive or limiting of the invention. The scope of the invention should be determined not with reference to the above description, but should be determined with reference to the appended claims, along with the full scope of equivalents to which such claims are entitled.

The terms "one embodiment", "an embodiment", "another embodiment", "some embodiments", "other embodiments", "above embodiments", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or", unless context clearly indicates otherwise.

The term "such as" is used herein to mean, and is used interchangeably, with the phrase "such as but not limited to". Unless specifically stated or obvious from context, as used herein, the term "about" is understood as within a range of normal acceptance in the art, for example within standard deviations of the mean.

The term "proximal" is herein used to mean a position or direction closest to a user of the device and is in a position or direction opposite to the term "distal".

The term "distal" is herein used to mean a position or direction furthest away from a user of the device and is a position or direction opposite to the term "proximal".

As used herein, the terms "chronic rhinosinusitis" or "CRS" can refer to the disease entity characterized by inflammation of the nasal cavity and/or paranasal sinuses lasting greater than about twelve weeks duration. Symptoms may include, but are not limited to: facial pain or pressure, nasal congestion or fullness, nasal obstruction or blockage, nasal discharge (rhinorrhea or post-nasal drip), hyposmia/anosmia, and purulence in the nasal cavity. Other potential symptoms include: headache, fever, halitosis, fatigue, dental pain, cough, and ear pain/pressure/fullness. In one example, the presence of severe inflammation and irritation with thickened discolored or purulent discharge can be indicative of CRS, whereas pale mucosa with clear discharge can be suggestive of allergic rhinitis. In another example, CRS can refer to recalcitrant forms of the disease in which symptoms persist despite medical or surgical treatment, as well as instances where patients cannot receive standard medical or surgical care due to contraindications for such care.

As used herein, the term "subject" or "patient" can refer to any warm-blooded organism including, but not limited to, human beings, pigs, rats, mice, dogs, goats, sheep, horses, monkeys, apes, rabbits, cattle, etc.

As used herein, the terms "treating" and "treat" can refer to therapeutically regulating, preventing, improving, alleviating the symptoms of, and/or reducing the effects or symptoms of CRS. The terms can also refer to chronic or acute treatment.

The terms "disorder", "disease", "condition", and similar language used herein refer to any situation deviating from normal.

The term "effective amount" used herein of a drug substance or formulation is an amount sufficient to bring about a desired result in a treated subject, for example, an amount sufficient to treat chronic rhinosinusitis in a subject in need. The effective amount may vary depending upon a particular formulation, the nature or severity of the condition being treated, the age, weight, and so on of a subject being treated, and other things. An effective amount can be readily determined by one skilled in the medical art.

The term "nasal" or "sinus cavities" refers to the various tissues defining the normally air-filled passages and chambers within the nose and sinus including but not limited to the nostrils or nares, the nasal concha or turbinates, the frontal, ethmoid, sphenoid and maxillary sinuses, the sinus ostia and the nasopharnyx, and to objects or articles (e.g., prostheses, packing or stents) that may be placed within a nasal or sinus cavity.

The term "magnetic particles" or "magnetic material" is used to indicate that they are attracted by a magnetic field or a magnet, not necessarily that they are permanent magnets. However, it is contemplated that either metallic or non-metallic permanent magnetic materials can alternatively be used for magnetic particles, and ceramic magnetic particles may have the advantage of being biologically inert.

The term "biocompatible" when used in reference to a substance means that the substance presents no significant deleterious or untoward effects upon the body of the subject.

The term "biodegradable" used herein in reference to a substance means that the substance will degrade or erode in vivo to form smaller chemical species. Such degradation process may be enzymatic, chemical or physical.

The term "bioresorbable" used herein in reference to a substance means that the substance is capable of being absorbed by the body of a subject.

The term "kit" as used herein refers to an assembly of items or materials or instructions that are used in performing a method as described herein. Such kits may include one or more of devices and/or components described herein.

All numeric values are herein assumed to be modified by the term "about" whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. Even more specifically, "about" can be understood as within 10%, 9%, 8%, 7%, 6%, 5%, 4%, 3%, 2%, 1%, 0.5%, 0.1%, 0.05%, or 0.01% of the stated value. Unless otherwise stated, all ranges include both endpoints and all numbers between the endpoints. The use of "about" or "approximately" in connection with a range applies to both ends of the range. Thus, "about 10 to 30" is intended to cover "about 10 to about 30", inclusive of at least the specified endpoints.

In one embodiment, the present disclosure provides a nasal implant configured to include magnetic particles deposited in a segment of the implant. The nasal implant is also configured to be attachable to a container, an injector, or a medical syringe.

In one embodiment, the present disclosure provides a nasal implant, the implant comprising a hollow structure having a distal end and a proximal end, the distal end configured to include magnetic particles, and the proximal end configured to be attachable to a container, an injector, or a medical syringe. In a preferred embodiment, the hollow structure is polymeric. In one embodiment, the distal end is configured to be covered with an outer layer coated with magnetic particles. In one embodiment, the distal end is configured to be covered with a separate layer coated with magnetic particles. In one embodiment, the distal end may be configured to be covered by a plurality of layers wherein at least one of the plurality of layers is covered with magnetic particles.

In one embodiment, the present disclosure provides a medical assembly for nasal implantation, the assembly comprising: a hollow implant having a distal end and a proximal end, the distal end configured to include magnetic particles; and a container, an injector, or a medical syringe configured to be attachable to the proximal end of the hollow polymeric implant. In an embodiment, the assembly further comprises a connector or adaptor configured to connect or engage the implant with the container, the injector, or the medical syringe. In a preferred embodiment, the hollow structure is polymeric.

In one embodiment, the present disclosure provides a drug delivery assembly for delivering a drug substance to a nasal cavity of a subject, the assembly comprising: a hollow implant having a distal end and a proximal end, the distal end configured to have one or more segments deposited with magnetic particles; and a container, an injector, or a medical syringe configured to be capable of retaining and transporting a magnetically active or magnetizable fluid composition containing the drug substance. In an embodiment, the assembly further comprises a connector or adaptor configured to connect or engage the implant with the container, the injector, or the medical syringe. In a preferred embodiment, the hollow structure is polymeric.

In one embodiment, the present disclosure provides a drug delivery assembly for delivering a drug substance to a nasal cavity of a subject, the assembly comprising: a hollow implant having a distal end and a proximal end, the distal end configured to have one or more segments deposited with magnetic particles; and a container, an injector, or a medical syringe configured to be attachable to the proximal end of the hollow implant wherein the container, the injector, or the medical syringe is also configured to be capable of retaining and transporting a magnetically active or magnetizable fluid composition containing the drug substance. In an embodiment, the assembly further comprises a connector or adaptor configured to connect or engage the implant with the container, the injector, or the medical syringe. In a preferred embodiment, the hollow structure is polymeric.

In the above embodiments, the nasal implant is sized and shaped for residence in a sinus or nasal cavity or passage without inhibiting the free passage of air, exhalation gases, mucus or other fluids into and out of the sinus or nasal cavity or passage. The nasal implant may be sized and shaped so as to just fit within such cavity or passage when uninstalled and unrestrained, or so as to be slightly compressed when installed in and restrained by such cavity or passage. Prior to installation, the nasal implant may be desirably compressed to a diameter suitable for loading into a handheld guidewire or inserter sized and shaped for delivery and insertion of the nasal implant into such cavity or passage.

More particularly, the hollow nasal implant has a distal end and a proximal end. For a frontal sinus implant, the distal end may preferably be configured to have a diameter of about 1 cm to about 3 cm. The distal end may be configured to have one or more segments deposited with magnetic particles. The segments may preferably be spaced from about 1 mm to about 30 mm. The overall length of the implant may preferably be configured to be between about 25 mm and about 50 mm. For a sphenoid sinus implant, the distal end may preferably be configured to have a diameter of about 3 mm to about 10 mm. The segments deposited with magnetic particles may preferably be spaced from about 1 mm to about 10 mm. The overall length of the implant may preferably be configured to be between about 10 mm and 25 mm. For a maxillary sinus implant, the distal end may preferably be configured to have a diameter of about 5 mm to about 20 mm. The segments deposited with magnetic particles may preferably be spaced to be about 1 mm to about 10 mm. The overall length of the implant may preferably be configured to be between about 15 mm and about 50 mm. In a preferred embodiment, the hollow structure is polymeric.

In some embodiments, the nasal implant includes a distal end configured to be in a straight shape. In some embodiments, the nasal implant includes a distal end configured to be in a curled shape. In some embodiments, the nasal implant includes a distal end configured to be in a pigtail shape. In some embodiments, the pigtail may be configured to have an open end. In some embodiments, the pigtail may have a closed end.

In the above embodiments, the distal end may be configured to have a plurality of pores, holes, or apertures. In some embodiments, the plurality of pores, holes, or apertures may be configured to vary in size or location or both. The plurality of pores, holes, or apertures may all be configured to be coated with magnetic particles. In some embodiments, only a portion of the plurality of pores, holes, or apertures may be configured to be coated with magnetic particles. In some embodiments, none of the plurality of pores, holes, or apertures is coated with the magnetic particles. Rather, the magnetic particles are coated outside of the plurality of pores, holes, or apertures in the distal end. In some embodiments, the entire distal end of the implant may be made with magnetic materials or rendered magnetic. In some embodiments, the distal end may be configured to be covered with an outer layer coated with magnetic particles. In some embodiments, the distal end may be configured to be covered with a separate layer coated with magnetic particles. In some embodiments, the distal end may be configured to be covered with a plurality of layers wherein at least one of the plurality of layers is coated with magnetic particles. In some embodiments, the magnetic particles may be optionally coated with a biocompatible coating. The magnetic particles may be any regular or irregular shape such as circular. The magnetic particles may preferably comprise a material that is attracted to magnetic field, such as a ferrous or rare earth metal or alloy.

In the above embodiments, the magnetic particles may be deposited onto the polymeric implant through known methods and techniques such as using paint brush, spraying airbrush, bonding a disk, sowing a disk, extruding a material, riveting a structure into a hole or forming a hole while planning a rivet.

In the above embodiments, the magnetic particles may be made from temporary magnetic materials or permanent magnetic materials. Some examples of suitable magnetic materials include magnetic ferrite which is a substance consisting of mixed oxides of iron and one or more other metals, the heat treatment of the mixed oxides producing complex crystals with magnetic properties. An example ferrite material is nanocrystalline cobalt ferrite. However, other ferrite materials may be possible. Other magnetic materials which may be utilized in the construction of the implant include but are not limited to: ceramic and flexible magnetic materials made from strontium ferrous oxide which may be combined with a polymeric substance such as plastic, or rubber; NdFeB (this magnetic material may also include dysprosium); SmCo (samarium, cobalt); and combinations of aluminum, nickel, cobalt, copper, iron, titanium as well as other materials.

In the above embodiments, the nasal implant includes a proximal end configured to include a straight tubular member. The diameter of the straight tubular member may be from about 1 Fr to about 8 Fr (1 Fr is equal to 3 mm). In some embodiments, the proximal end of the nasal implant includes a fitting lock configured to be attachable to a container, an injector, or a medical syringe. The fitting lock may be made by known methods in the art. For example, the fitting lock may be configured to have a ring magnet. The ring magnet is configured such that it can receive another ring magnet installed at the distal tip of a syringe to seal the connection between the syringe and the implant.

In some embodiments, the whole nasal implant may be configured to be a straight shape. Additionally or alternatively, the nasal implant may have a malleable property, and can have the shape adjusted after implantation. It may also have shape memory properties (such as composed of Nitinol) which allows for its shape to assume a predetermined shape after implantation. Use of inserts made of materials which have shape memory properties permit the implant to assume a preset shape after insertion. Alternately, certain conditions may be applied, such as application of heat, cold, light, or a magnetic field, that will allow the material to assume a desired fixed or modified shape after implantation. The necessary condition will depend on the intrinsic properties of the shape memory material chosen to produce the implant. The fixed shape of the implant may also be adjusted before or after insertion. In some embodiments, the nasal implant described herein may be drug-eluting or non-drug-eluting. The drug eluting implant is pre-loaded with a drug during its manufacture or through methods known in the art.

It is understood that the implant is to be inserted into a nasal cavity, and must therefore be biocompatible. The broad term biocompatible includes nontoxicity, noncarcinogenity, chemical inertness, and stability of the material in the living body. Exemplary biocompatible materials are titanium, alumina, zirconia, stainless steel, cobalt, and alloys thereof. Unfortunately, some magnetic materials may not be sufficiently biocompatible to be suitable for use in an implant construction. To avoid problems associated with non-biocompatible materials, where the magnetic particles are from a magnetic material which is non-biocompatible, the magnetic particles may be coated with a biocompatible coating. Biocompatible coatings for use with implants are well known, and an example of such a coating may be gold. However, any biocompatible coating may be used with the present disclosure.

In the above embodiments, the nasal implant may be biodegradable or not biodegradable. The rate of degradation of the biodegradable implant is determined by factors such as configurational structure, copolymer ratio, crystallinity, molecular weight, morphology, stresses, amount of residual monomer, porosity and site of implantation. The skilled person will be able to choose the combination of factors and characteristics such that the rate of degradation is optimized. In some embodiments when the implant is not biodegradable, a physician may be allowed to stop the therapy when he desires rather than letting the implant break down by itself. In some embodiments, the polymers used for the nasal implant may be non-biodegradable. Examples of preferred non-biodegradable polymers include poly ethylene vinyl acetate (EVA), poly(meth)acrylic acid, polyamides, silicone-based polymers and copolymers and their mixtures.

In some embodiments, the polymeric implant may be configured to have a net or cage like structure at its distal end to capture any or all spheres injected through the center of the tubular implant. The cage or net like structure may be a sponge type of material that absorbs the media and release over time. The polymeric implant may also be configured to include a drug substance that is incorporated into the implant during its manufacturing process. The drug substance may be the same as the one that is to be transport by a medical syringe. The drug substance may be a different one.

In the above embodiments, the container, the injector, and the medical syringe are interchangeably used to illustrate a device capable of retaining and transporting a fluid. Other similar devices are also contemplated so long as they are capable of retaining and transporting fluid substances. More particularly, the present disclosure is concerned about using a device to contain and transport magnetically active fluid composition. The fluid composition may contain spheres which are magnetically active. For simplicity of present disclosure, a syringe will be used as an exemplary device for this purpose. It is well known that syringes are capable of storing and transporting substances with fluid properties such as gases, liquids, pastes, slurries, or any other material that tends to flow in response to applied shear stress. A syringe may include a barrel defining a bore in communication with a port, and a plunger disposed within the barrel. Translation of the plunger away from the port may draw material into the barrel through the port. Alternatively, translation of the plunger toward the bore may expel material from the barrel out of the port.

A syringe barrel may be formed from a transparent or translucent material, such that a position of the plunger within the bore is visible through the barrel. Further, the syringe barrel may include indicia disposed thereon, such that longitudinal alignment of the plunger relative to the indicia may visually indicate a volume of material stored within the syringe.

In an embodiment, the medical syringe is configured to have a fixed elongated tip. In an embodiment, the fixed elongated tip is configured to be suitable for insertion into the distal end of the nasal implant as described herein. In an embodiment, the medical syringe is configured to be attachable to an adaptor or a connector. In an embodiment, the adaptor or the connector is configured to be attachable to the nasal implant described herein. In an embodiment, the adaptor or the connector is configured to be suitable for insertion into a nasal cavity. In an embodiment, the adaptor or the connector may be made re-usable or disposable. In an embodiment, the medical syringe has a plunger which is designed to have a pin at its distal end for dislodging the implant from the syringe.

In the above embodiments, the medical syringe may be employed to retain and transport a magnetically active fluid composition. In the above embodiments, the medical syringe may be employed to retain and direct the magnetically active fluid composition through the nasal implant to be accumulated around the magnetic particles of the nasal implant.

The medical syringe may be formed from a variety of materials including but not limited to flexible, rigid or semi-rigid polymeric materials, glass, metals and alloys thereof, and the like, and combinations thereof. The medical syringe may be configured to be squeezable and/or pressurized to facilitate delivery of the magnetically active or magnetizable fluid composition containing a drug substance through the barrel into the implant. In some embodiments, the syringe may be made disposable or re-usable. The method of making the syringe as described herein is well known in the art.

In some more specific embodiments, two types of magnetically active fluid compositions or spheres are contemplated for drug delivery purpose. The first type combines a therapeutic drug with a plurality of metallic particles that are suspended in an aqueous solution such as saline to create a magnetic fluid. The second type of magnetic fluid employs metallic magnetically attracted particles that are coated with a polymeric material. The polymeric coating is selected for its ability to bind a therapeutic drug directly to the magnetic particles by adsorption, which is reversible. The coated and bound metallic particles are suspended in a solution such as saline. When either type of magnetic fluid is injected into the patient's body, it is attracted by the magnetic particles deposited at the distal end of the polymeric implant to the treatment site, thereby concentrating the therapeutic drug at the site.

In a preferred embodiment, the magnetic fluid composition is the type in which the drug substance is bound to a polymeric coating that encapsulates magnetic materials in a fluid suspension. It will be appreciated that where the magnetic particles are more heavily concentrated, the drug substance bound to the magnetic materials is also highly concentrated. Furthermore, because the magnetically active fluid composition is attracted to the magnetic particles, the drug substance is much less likely to be carried away from the treatment site.

In the above embodiments, the drug substance may be anti-inflammatory agents such as mometasone furoate, anti-proliferation agents such as paclitaxel or everolimus, antibiotics, and other medications.

In the above embodiments, the amount of the drug substance delivered in accordance with the present disclosure can be readily determined by one of ordinary skill in the art and will vary according to factors such as the nature and/or concentration of the drug substance, the patient's age, condition, and/or sensitivity to the drug substance, and the like.

In an embodiment, the present disclosure provides a method of treating chronic rhinosinusitis of a subject. In an embodiment, the present disclosure provides a method of treating inflammation of the nasal cavity and paranasal sinuses of a subject. In another embodiment, the present disclosure provides a method of treating inflammation of a nasal cavity and paranasal sinuses of a subject by concentrating a drug substance around the nasal cavity that needs treatment. In an embodiment, the present disclosure provides a method of enhancing accumulation of a drug substance around a nasal cavity of a subject.

In an embodiment, treating CRS is to reduce sinus inflammation. In an embodiment, treating CRS is to keep the nasal passages draining. In an embodiment, treating CRS is to eliminate the underlying cause. In an embodiment, treating CRS is to reduce the number of sinusitis flare-ups. In an embodiment, treating CRS is to relieve inflammation from severe sinusitis.

In the above embodiments, the method comprises providing a nasal implant configured to include magnetic particles. The method also comprises providing a medical syringe configured to be capable of retaining a magnetically active fluid composition. The method further comprises providing a magnetically active fluid composition containing spheres. The method may optionally comprise providing a connector or adaptor configured to connect or engage the nasal implant with the medical syringe. The method also comprises providing any accessories deemed necessary for a delivery of the nasal implant into a nasal cavity. In an embodiment, the method may optionally include the step of removing the nasal implant from the patient's nasal cavity after the desired therapy has been achieved. In an embodiment, the method may also include repeating all the above steps one or more times for a period of one to two weeks. In an embodiment, the method may also include repeating all the above steps one or more times for a period of one to two months. In an embodiment, the method may also include repeating all the above steps one or more times whenever necessary.

In the above embodiments, the method of treating chronic rhinosinusitis of a subject includes the steps of: positioning a nasal implant in a nasal cavity; delivering a magnetically active fluid composition to the nasal implant wherein the magnetically active fluid composition contains a pharmaceutically active drug substance.

In the above embodiments, the method of treating chronic rhinosinusitis of a subject includes providing a nasal implant comprising a hollow polymeric structure having at least a segment deposited with magnetic particles; providing a medical syringe configured to be capable of retaining and transporting a magnetically active fluid composition containing a drug substance; inserting the nasal implant into a nasal cavity; engaging the nasal implant with the medical syringe; loading the medical syringe with the magnetically active fluid composition; and transporting the magnetically active fluid composition through the nasal implant to provide substantially concentrated drug substance at the nasal cavity.

In the above embodiments, the method of enhancing accumulation of a drug substance in a nasal cavity includes providing an implant configured to have a distal end deposited with magnetic particles; providing a medical syringe configured to be capable of retaining and transporting a magnetically active fluid composition containing a drug substance; inserting the implant into a nasal cavity; connecting or engaging the implant with the medical syringe; loading the magnetically active fluid composition into the medical syringe; and pushing the fluid composition through the medical syringe to provide increased concentration of the drug substance at the nasal cavity.

In the above embodiments, the method of concentrating a drug substance at a nasal cavity of a patient includes providing a nasal implant comprising a hollow polymeric structure having at least a segment deposited with magnetic particles; providing a container or a medical syringe configured to be capable of retaining and transporting a magnetically active fluid composition containing a drug substance; providing the magnetically active fluid composition containing the drug substance; inserting the nasal implant into a nasal cavity; loading the magnetically active fluid composition into the medical syringe; squeezing the fluid composition through the medical syringe to provide substantially increased concentration of the drug substance at the nasal cavity.

Generally, the nasal implant may be inserted in a similar fashion regardless of the site or the disease being treated. Briefly, a pre-insertion examination may be conducted by direct visualization, possible endoscopy, and rarely diagnostic imaging. The areas of structural defects, volume defects, of dynamic collapse of the nose are noted. The implant size and material is selected to suit the particular application, where more than one implant material and size may be available.

In the above embodiments, the nasal implants may be maneuvered into place directed by visual and tactile control. In certain aspects, the implant may further include a radio-opaque, echogenic material, or MRI responsive material (e.g., MRI contrast agent) to aid in visualization of the device under ultrasound, fluoroscopy and/or magnetic resonance imaging. The radio-opaque or MRI visible material may be in the form of one or more markers (e.g., bands of material that are disposed on either end of the implant). For example, the implant may be delivered to a nasal cavity site through a guidewire whereby the implant may slide over the guidewire and be released through methods well known in the art.

In the above embodiments, the medical syringe may be connected or engaged with the implant through known methods of connecting a syringe to a tube, such as magnet on a syringe tip and another magnet on the tube. To release the tube the plunger can include a rod that would kick off the tube with the magnet at the end of the stroke of the syringe.

In the above embodiments, the nasal implant having magnetic particles will attract a magnetically active fluid composition at the treatment site due to magnetic attractions. In this way, a magnetic fluid composition that includes a drug substance can be selectively targeted and concentrated in the treatment site within a nasal cavity of a patient.

In a further embodiment, the present disclosure provides a kit for performing a method as described herein. The kit includes a nasal implant, a medical syringe, a magnetically active fluid composition containing a drug substance, and other accessories and instructions for delivering the implant and the fluid composition into a nasal cavity.

In an embodiment, treating CRS as described herein provides local and sustained drug delivery in the sinus of a patient as an alternative treatment option to sinus surgery. Such a treatment may establish safe and effective sustained drug delivery localized to the inflamed area and in some case may prevent the need for surgery. In an embodiment, treating CRS as described herein may be used as a supplemental therapy in addition to a surgery.

In another embodiment, the present disclosure also provides a method of treating chronic rhinosinusitis of a subject, comprising providing a nasal implant comprising a hollow polymeric structure having at least a segment deposited with magnetic particles; providing a container, an injector, or a medical syringe configured to be capable of retaining and transporting a magnetically active fluid composition containing a drug substance; inserting the nasal implant into a nasal cavity; connecting the nasal implant with the container, the injector, or the medical syringe; supplying the magnetically active fluid composition to the nasal cavity to provide substantially increased concentration of the drug substance at the nasal cavity.

The principles of the present disclosure may be better understood with reference to the drawings and the accompanying descriptions, wherein like reference numerals have been used throughout to designate identical or similar elements. It should be understood that these drawings are not necessarily are drawn to scale. They are presented just for illustrative purposes only, and are not intended to limit the scope of the disclosure. Examples of materials, dimensions, and constructions are included for some elements. Those of ordinary skill in the art should understand that many of the examples provided have suitable alternatives and these alternatives should also be considered within the scope of this disclosure. Moreover, certain terminology is used herein for convenience only and is not to be taken as a limitation on the present disclosure.

The human nose has right and left nostrils or nares that lead into separate right and left nasal cavities. The right and left nasal cavities are separated by the intranasal septum, which is formed substantially of cartilage and bone. Posterior to the intranasal septum, the nasal cavities converge into a single nasopharyngeal cavity. Paranasal sinuses are formed in the facial bones on either side of the face. The paranasal sinuses open, through individual openings or ostia, into the nasal cavities. The paranasal sinuses include frontal sinuses, ethmoid sinuses, sphenoidal sinuses, and maxillary sinuses.

Figure 1:
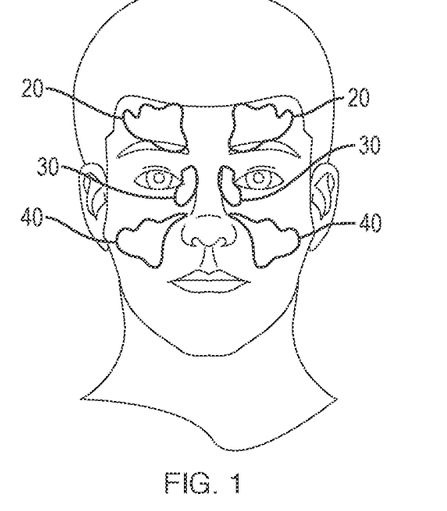
FIG. 1 is a schematic view of human anatomical tissue structures including the maxillary, frontal, and ethmoid sinus cavities.
Figure 2A:
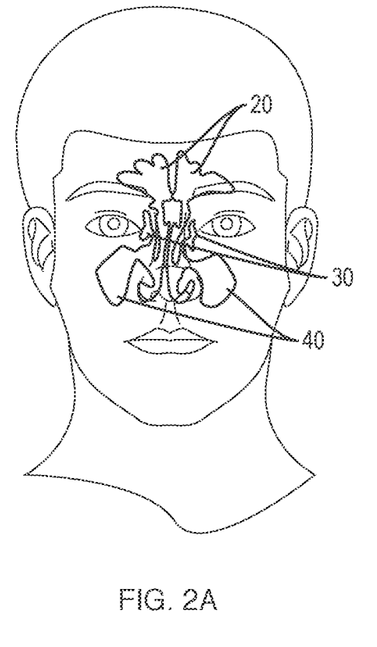
FIG. 2A is a frontal view of a human head showing the locations of the paranasal sinuses.
Figure 2B:
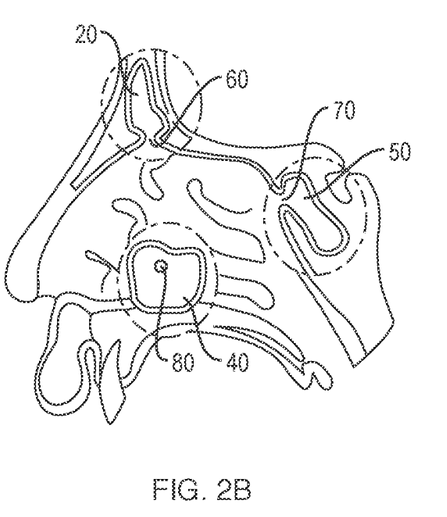
FIG. 2B is a side view of a human head showing the locations of the paranasal sinuses.

More particularly, FIGS. 1, 2A and 2B illustrate anatomical structures associated with human sinuses from different perspectives. There are four different pairs of sinuses: the frontal sinuses 20; the ethmoid sinuses 30; the maxillary sinuses 40; and the sphenoid sinuses 50 (FIG. 2B, located more toward the back of the head than the other sinuses). FIG. 2B further illustrates frontal sinus ostium 60, sphenoid sinus ostium 70, and maxillary sinus ostium 80. Normally, these sinuses are filled with air, but when one or more of these sinuses become blocked and filled with fluid, pathogens can grow and cause an infection. The factors that contribute to the sinus initially becoming blocked off are likely multi-factorial, but may be due to infections, inflammation, allergy, immunologic abnormalities, or other processes.

Figure 3:
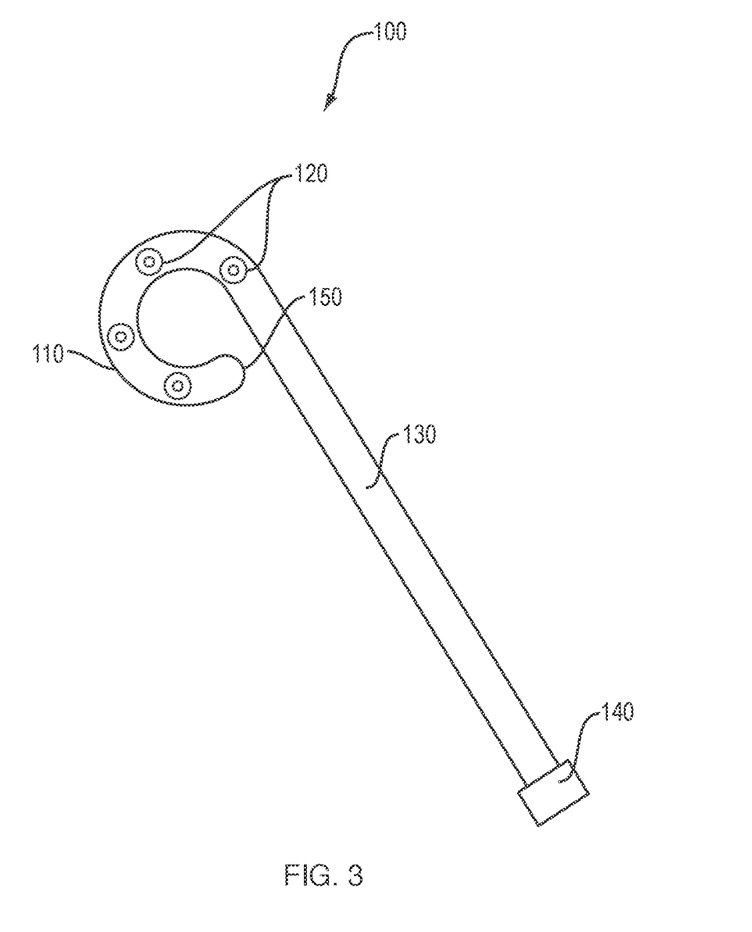
FIG. 3 is a schematic view of a nasal implant in accordance with one aspect of the present disclosure.

FIG. 3 is a schematic view of a nasal implant 100 in accordance with one aspect of the present disclosure. The nasal implant 100 may be preferably made of polymeric materials. Other suitable biocompatible materials are also contemplated. The nasal implant 100 of FIG. 3 shows curled or pigtailed distal end 110. The curled end 110 comprises segments deposited with magnetic particles 120. The segments may be configured to be equally spaced. The segments may be configured to be unequally spaced. The curled end 110 may further comprise pores or holes or apertures. These pores or holes or apertures may be configured to be evenly distributed or unevenly distributed around the distal end. They may be called homogeneous if those pores, holes or apertures are substantially evenly distributed. They may be called heterogeneous if those pores, holes or apertures are not substantially evenly distributed. These pores or holes or apertures may be configured to be coated with magnetic particles. The sizes of these pores or holes or apertures may be configured to be the same or different. The curled distal end is generally tubular. The length of the curled portion 110 may vary depending on its purpose of use for different nasal cavities. The implant 100 also includes a stem 130, and its length may also vary depending on its purpose of use for different nasal cavities. The stem 130 has a locking fitting 140 at its proximal end. The stem 130 may be configured to be straight. The stem 130 may generally be configured tubular. The locking fitting 140 may be configured to have magnetic property for its easy docking with the tip of a syringe such as having a ring magnet. It may also be configured to have an easy snap fit feature for its connection with the tip of a syringe under the guidance of an endoscope. It is also contemplated that the proximal end of the implant may not need a locking fitting if an elongated syringe can be inserted to the distal end of the nasal implant.

The curled distal end 110 may be configured to have an open end which allows a fluid to flow out from the farthest distal end. The curled distal end 110 may be configured to have a closed end which will then force a fluid to flow out through the pores, holes or apertures installed around the distal end. Once the magnetically active fluid composition flows through the stem 130 of the implant into the curled portion, the fluid composition will flow out through the holes, pores, or the apertures. Since the pores, holes or apertures are coated with magnetic particles, the magnetically active liquid composition containing a drug substance will then be absorbed or concentrated onto the magnetic particles due to magnetic attractions, thereby keeping the drug substance around the magnetic particles for a prolonged period of time. As a result of this concentration, the treatment result is expected to be significantly improved.

In some aspects, the implant 100 may also be configured to contain a pre-loaded drug substance. The pre-loaded drug substance may be the same as the one that is to be injected through the syringe as described herein. The pre-loaded drug may be different from the drug substance that is to be injected. In some aspects, the whole implant 100 may be pre-loaded with a drug substance. In some situations, only the distal end 110 may be pre-loaded with a drug substance. The implant may be designed to be delivered in compressed form into a nasal cavity as is or following functional endoscopic sinus surgery ("FESS"), whereupon it may expand, slowly degrade, elute the drug substance to nearby tissues, and can help treating conditions such as chronic rhinosinusitis.

Figure 4A:
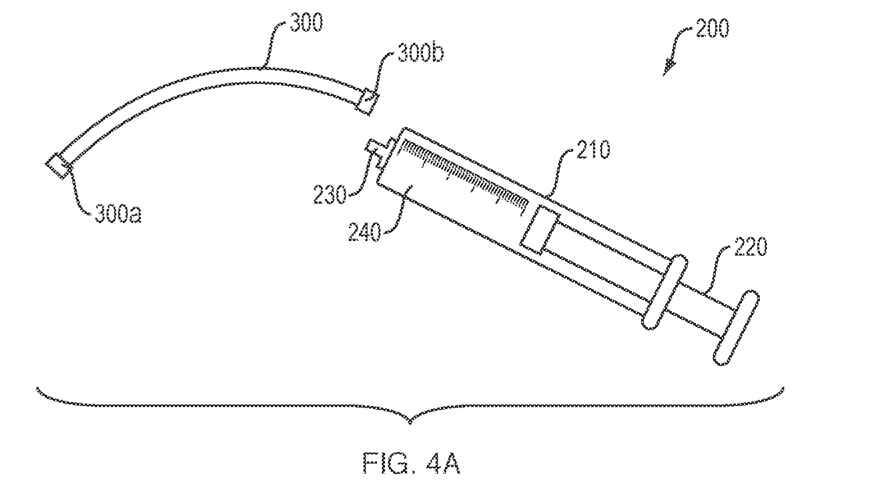
FIG. 4A is schematic view of a medical syringe in accordance with one aspect of the present disclosure.
Figure 4B:
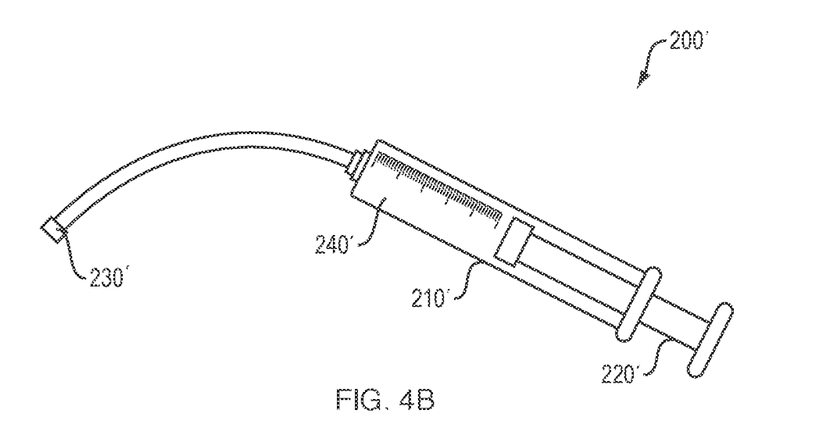
FIG. 4B is schematic view of a medical syringe in accordance with another aspect of the present disclosure.
Figure 4C:
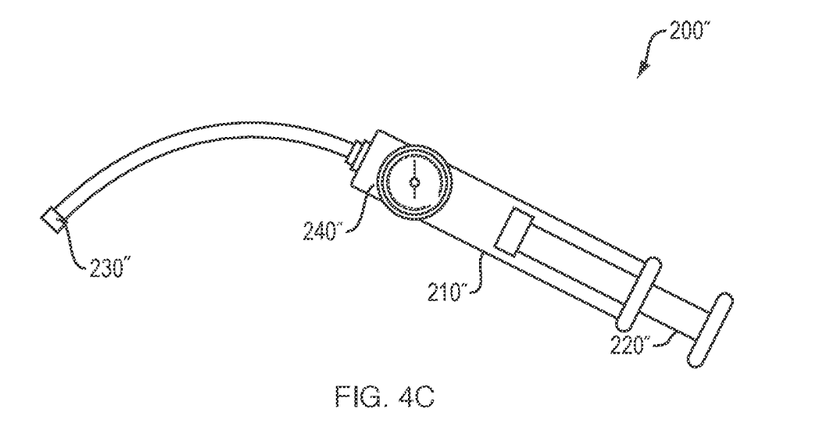
FIG. 4C is schematic view of a medical syringe in accordance with yet another aspect of the present disclosure.

FIGS. 4A, 4B, and 4C are schematic views of a syringe and related adaptor or connector in accordance with the present disclosure. FIG. 4A shows a syringe 200 including a barrel 210, a plunger 220, and an open tip or port 230 at the distal end. The barrel has a chamber 240 configured to retain/store magnetically active fluid composition containing a drug substance. The open tip 230 of the syringe 200 may be configured to be connectable with an independent connector or adaptor 300. The connector or adaptor 300 is configured to have two open ends: one end 300*b* for connection with the open tip 230 of the syringe 200, the other end 300*a* for connection with the locking fitting 140 of the implant 100 as described for FIG. 3. The connector 300 may be configured to be flexible or semi-flexible and resilient or strong enough to be able to traverse through nasal cavities. The end 300*a* may be configured to have magnetic property such as a ring magnet which will facilitate its docking with the locking fitting 140 of the implant 100.

Alternatively or additionally, the connector or adaptor portion of the syringe 200 may be configured to be a permanent part of the syringe 200' as shown in FIG. 4B. The barrel 210' may be configured to have graduated marks indicating the volume of the liquid inside the chamber 240'. The extended portion of the syringe 200' may be configured to be flexible or semi-flexible and resilient or strong enough to be able to traverse through nasal cavities. The end 230' may be configured as a blunt type of tip so that it may be able to traverse under endoscopic guidance or other guiding methods all the way through to the curled distal end of the implant 100 to be close to the pores coated with magnetic materials to facilitate concentration of a drug substance. Making the tip blunt or at least not sharp may avoid any potential damage that may be caused by a sharp tip's accident contact with nasal tissues.

Alternatively or additionally, a syringe may be configured to be a syringe 200" as shown in FIG. 4C wherein the plunger 210" is equipped with a pressure or volume measuring device to measure the pressure or volume of the liquid to be delivered. The other aspects of the syringe 200" are identical or significantly similar to those of the syringe of 200' as shown in FIG. 4B.

The syringe 200, or 200', or 200" may be formed from a variety of materials including but not limited to flexible, rigid or semi-rigid polymeric materials, glass, metals and alloys thereof, and the like, and combinations thereof. It is configured to be squeezable and/or pressurized to facilitate delivery of the magnetically active or magnetizable spheres or fluid composition containing a drug substance through the barrel into the implant. In some embodiments, it may be made disposable or re-usable. The method of making the syringe as described herein is well known in the art.

Figure 5A:
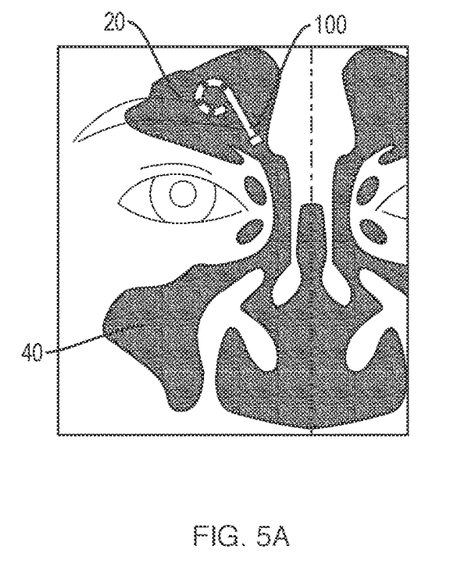
FIG. 5A is a schematic view of a nasal implant disposed inside a frontal sinus in accordance with one aspect of the present disclosure.
Figure 5B:
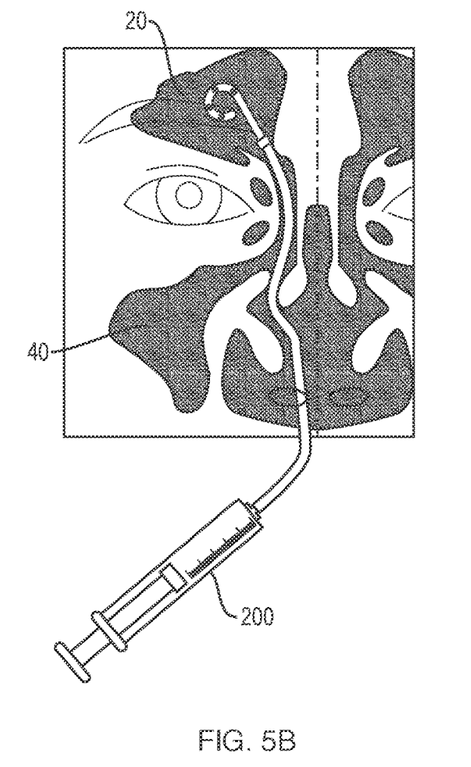
FIG. 5B is a schematic view of a nasal implant connected with a medical syringe in accordance with another aspect of the present disclosure.

FIG. 5A shows an implant 100 disposed inside a frontal sinus 20 of a patient. The insertion of the implant 100 may be accomplished by known methods such as through ultrasonic guidance or through an endoscope. In one aspect, once the implant 100 is placed into proper position, a syringe may subsequently be engaged or locked with the implant as shown in FIG. 5B. More particularly, FIG. 5B shows the proximal end of the implant 100 is engaged or locked with the tip end of a syringe 200. The engagement or locking may be achieved through known methods. For example, the proximal end of the implant may be configured to have a ring magnet or snap fit feature, and the elongated tip end of the syringe may also be configured to have a ring magnet or snap fit feature. Once the elongated tip of the syringe is brought close to the proximal end, it will be easily attracted or manipulated into a proper locking or engaging position due to magnetic attraction or snap-fitting. The elongated tip of the syringe may be configured to be a permanent part of the syringe, or be a detachable tip end. The elongated tip of the syringe should be made to be strong, flexible, and resilient. Once the locking or engaging between the implant and the syringe is properly achieved, the syringe may then be loaded with a magnetically active fluid composition, and the fluid composition pushed through the barrel of the syringe, and into the stem of the implant, and flow out of the holes at the distal end of the implant. The magnetically active fluid composition will then be concentrated around the distal end due to magnetic attraction between the fluid composition and the magnetic particles at the distal end. The attraction force between the two magnets is configured to be enough to facilitate the delivery of the magnetic fluid and yet allowing easy separation by a hand pull. Also, it may be pushed apart by a rigid rod from inside the barrel of the syringe. It may also be disengaged or dislodged by other means known in the art such as using guidewire and endoscope. These techniques should be easily understandable and performed by a skilled person in the field. This loading and transporting process may be repeated as needed until a desired condition is achieved.

Figure 5C:
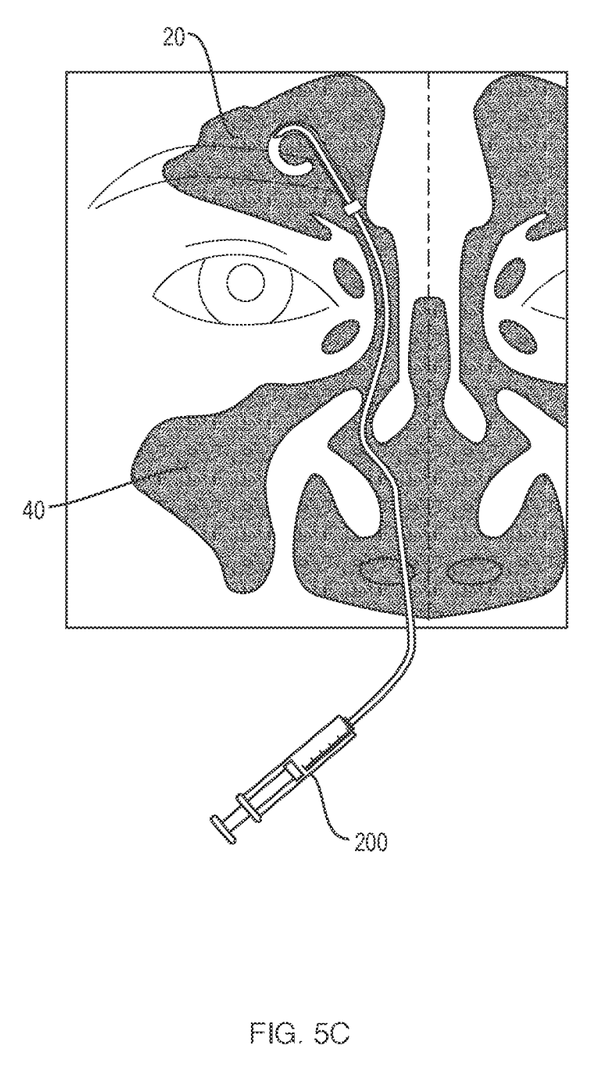
FIG. 5C is a schematic view of a nasal implant connected with a medical syringe in accordance with yet another aspect of the present disclosure.

In another aspect, once the implant is put into proper position inside a nasal cavity such as a frontal sinus, a syringe as described herein can then be engaged with the implant as shown in FIG. 5C. The syringe as shown in FIG. 5C may have a fixed elongated tip inserted all the way to the distal end of the implant. The syringe may be connected to an adaptor to reach to the distal end of the implant. The syringe, either with a fixed elongated tip or through a connector, does not have to have a locking or sealing relationship. Rather, it only has to be capable of being insertable into the distal end of the implant under endoscopic or other proper guidance. Once the implant and the syringe are placed into proper positions, the syringe may then be used to transport a magnetic fluid through the barrel of the syringe at a flow rate as desired. It is contemplated that once the fluid flows out of the tip of the syringe, it will flow out of the implant through the holes distributed around the distal end of the implant. Once that happens, the drug substance contained in the magnetic fluid will be concentrated through magnetic attractions around the distal end where there are deposited magnetic particles. More specifically, once a magnetically active fluid composition containing a drug substance is loaded into the barrel of the syringe, the fluid composition will then be pushed through the barrel and out into the distal end of the implant.

All the components as described in the above figures are preferably dimensioned so that proper engagement or connection therebetween occurs to form an operable relationship between the implant and the syringe such that magnetically active fluid composition may be desirably transported from the syringe to a nasal cavity through the nasal implant.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed:

1. An indwelling device configured for implantation in a nasal sinus cavity, the device comprising:
   a hollow polymeric catheter having a distal portion and a proximal portion, the catheter including pores only in the distal portion, the distal portion including a sponge material that releases an infused fluid drug substance at the distal portion over time and into the nasal sinus cavity to treat chronic rhinosinusitis (CRS), and a proximal end of the proximal portion attachable to a medical syringe, the fluid drug substance infused with magnetic particles; and
   a magnetic particle coating around the pores targeting and concentrating the drug substance at and around the nasal sinus cavity by magnetic attractions to the magnetic particles of the infused fluid drug substance to treat the CRS.

2. The implantable device of claim 1, wherein the magnetic particle coating is external to the catheter.

3. The implantable device of claim 1, wherein only a portion of the pores are coated with the magnetic particle coating.

4. The implantable device of claim 1, wherein the distal portion includes a curled or pigtail shape.

5. The implantable device of claim 1, wherein the distal portion includes an open or closed end.

6. An at least partially implantable medical assembly configured for implantation in a sinus cavity, the assembly comprising:
   an indwelling implant having a hollow polymeric catheter having a distal portion and a proximal portion, the catheter including pores only in the distal portion, a sponge material in the distal portion that absorbs a liquid drug substance and releases the drug substance over time in the distal portion to treat chronic rhinosinusitis (CRS), and first magnetic particles coated around the pores, the liquid drug substance infused with second magnetic particles, the first magnetic particles configured to target and concentrate the liquid drug substance at and around the nasal sinus cavity by magnetic attractions to the second magnetic particles to treat the CRS; and
   a medical syringe configured to be attachable to a proximal end of the proximal portion of the catheter and to provide the liquid drug substance.

7. The medical assembly of claim 6, wherein the assembly further comprises a connector configured to connect the implant and the medical syringe.

8. The medical assembly of claim 6, wherein the medical syringe is configured to have a fixed elongated tip.

9. A method of treating chronic rhinosinusitis (CRS) of a patient, comprising:
   providing an indwelling implantable device including a hollow polymeric catheter having a distal portion and a proximal portion, the catheter including pores only in the distal portion, a sponge material in the distal portion that absorbs a liquid drug substance and releases the drug substance over time in the distal portion to treat CRS and a magnetic particle coating around the pores;
   providing a medical syringe configured to retain a magnetically active fluid composition containing a drug substance; and
   transporting the magnetically active fluid composition to a nasal cavity of the patient to target and concentrate the drug substance at or around a nasal sinus cavity of the patient by magnetic attractions between the magnetically active fluid composition and the magnetic particle coating to treat the CRS.

10. The method of claim 9, wherein the drug substance includes an anti-inflammatory agent.

11. The method of claim 9, wherein the drug substance includes mometasone furoate.

12. The method of claim 9, further comprising adjusting a shape of the implantable device by:
   traversing an insert into the implantable device to adjust the shape of the implantable device;

applying heat to the implantable device to adjust the shape of the implantable device;

applying cold to the implantable device to adjust the shape of the implantable device; or applying light, to the implantable device to adjust the shape of the implantable device.

13. The method of claim 9 further comprising before implanting the implantable device, pre-loading the implantable device with a second drug substance.

14. The method of claim 13, wherein the second drug substance is different from the drug substance.

15. The method of claim 13, wherein pre-loading the implantable device includes pre-loading only the distal end of the implantable device with the drug substance.

16. The method of claim 9, wherein the magnetic particle coating is non-biocompatible and the magnetic particle coating is coated with a biocompatible coating.

17. The method of claim 9 further comprising inserting the medical syringe into the implantable device to the distal end of the implantable device.

18. The method of claim 9 further comprising forcing, by a closed distal end of the implantable device, the magnetically active fluid composition through the pores.

* * * * *